United States Patent [19]

Henrick

[11] Patent Number: 5,648,562
[45] Date of Patent: Jul. 15, 1997

[54] OXIDATION PROCESS

[75] Inventor: Clive A. Henrick, Palo Alto, Calif.

[73] Assignee: Sandoz Ltd., Basel, Switzerland

[21] Appl. No.: 453,841

[22] Filed: May 30, 1995

Related U.S. Application Data

[63] Continuation-in-part of Ser. No. 378,292, Jan. 25, 1995, abandoned, which is a continuation-in-part of Ser. No. 285,263, Aug. 3, 1994, abandoned.

[51] Int. Cl.$^6$ .................................................. C07C 39/24
[52] U.S. Cl. .................................................. 568/774
[58] Field of Search .................................................. 568/774

[56] References Cited

U.S. PATENT DOCUMENTS

| | | |
|---|---|---|
| 3,130,007 | 4/1964 | Dreck . |
| 3,308,069 | 3/1967 | Wadlinger et al. . |
| 3,702,882 | 11/1972 | Rettew . |
| 3,992,466 | 11/1976 | Plank et al. . |
| 4,086,186 | 4/1978 | Rubin et al. . |
| 4,257,885 | 3/1981 | Grose et al. . |
| 4,410,501 | 10/1983 | Taramasso et al. . |
| 4,568,777 | 2/1986 | Baltes et al. . |
| 4,670,610 | 6/1987 | Sehring . |
| 5,003,114 | 3/1991 | Custantini et al. . |
| 5,055,623 | 10/1991 | Gabelmann et al. . |
| 5,098,687 | 3/1992 | Skeels et al. . |
| 5,110,995 | 5/1992 | Kharitonou et al. . |
| 5,233,097 | 8/1993 | Nemeth et al. .......................... 568/803 |

*Primary Examiner*—Samuel Barts
*Attorney, Agent, or Firm*—Lynn Marcus-Wyner

[57] ABSTRACT

Process for oxidizing 1,4-dichlorobenzene using a secondary synthesized zeolites or zeolite-like metallosilicates or a primary synthesized zeolite-like metallosilicate and a peroxide.

20 Claims, No Drawings

OXIDATION PROCESS

The present invention is a Continuation-In-Part of application Ser. No. 08/378,292, filed Jan. 25, 1995, which is a Continuation-In-Part of application Ser. No. 08/285,263, filed Aug. 3, 1994, both now abandoned.

The present invention concerns the selective oxidation of 1,4-dichlorobenzene to 2,5-dichlorophenol.

U.S. Pat. No. 5,233,097 describes in general a process for oxidation of aromatics using aluminosilicates containing framework titanium. No mention is made of oxidation of 1,4-dichlorobenzene. Additionally Romano et al. Chim. Ind. 72 p 610–616 (1990) state that substrates bearing electron-withdrawing substituents, such as chlorobenzene, cannot be oxidized to the corresponding phenols using a titanium silicalite such as TS-1 as the catalyst.

It has now surprisingly been found that oxidation employing molecular sieves of this type is particularly suited to the selective oxidation of 1,4-dichlorobenzene. Unexpectedly, this selective oxidation of 1,4-dichlorobenzene to 2,5-dichlorophenol is superior to the oxidation of other isomers and allows use of the 2,5-dichlorophenol to prepare high purity end-products.

The present invention therefore provides a process for the preparation of 2,5-dichlorophenol which comprises selectively oxidizing 1,4-dichlorobenzene using a peroxide in the presence of a catalyst selected from a secondary synthesized zeolite or zeolite-like metallosilicate; a primary synthesized zeolite-like metallosilicate; or an aluminophosphate based molecular sieve.

In its most commonly used form the term zeolite refers to crystalline alumino-silicates which act as molecular sieves. Zeolite-like substances are microporous crystalline materials with a framework forming regularly shaped channels and/or cages of specific molecular dimensions. These channels and cages contain water which, upon heating, can be desorbed without collapse of the structure. It will be appreciated that this description of zeolite-like materials also encompasses true zeolites. The channels created in the materials determine the suitability of a particular catalyst for a particular reaction as the starting materials should be capable of entering into the channels. Further description of zeolite and zeolite-like materials and their use can be found in e.g. Weitkamp et al., Royal Society of Chemistry Special Publication no. 97 pp 326–347 (1991); Davis et al. in Characterization of Catalytic Material, Wachs, I. E. (Ed.) Butterworth-Heinemann pp 129–148 (1992); Davis Ind. Eng. Chem. Res. v. 30 pp 1675–1683 (1991); Robo in Derouane et al. (Eds) Zeolite Microporous Solids, Kluwer pp 531–54 (1992); Szostak, Molecular Sieves: Principles of Synthesis and Identification; van Nostrand Reinhold, New York (1989).

The substitution of ions other than $Al^{3+}$ and $Si^{4+}$, such as titanium, vanadium, iron, boron, chromium, beryllium, gallium, cobalt, zinc and the like, in pure silica or aluminosilicate frameworks produces molecular sieves normally called metallosilicates. Additional elements may also be incorporated into the aluminophosphate based molecular sieves. Such elements include silicon, magnesium, iron, titanium, cobalt, vanadium, zinc, manganese, gallium, gemanium, beryllium and boron.

The catalysts used in the practice of this invention therefore comprise three main categories, secondary synthesized zeolites and zeolite-like metallosilicates; primary synthesized zeolite-like metallosilicates; and aluminophosphate based molecular sieves.

Secondary synthesized zeolites or zeolite-like metallosilicates according to the invention are crystalline aluminosilicates or other metallosilicates that have one or more additional metals such as titanium, vanadium or iron present as framework oxide units. These are prepared e.g. by contacting a zeolite with a suitable salt e.g. a fluoro ammonium or nitrate salt of the desired substitute metal (e.g. titanium, vanadium or iron) such that framework aluminum is replaced to the desired extent by the substitute metal (cf U.S. Pat. No. 5,098,687 and U.S. Pat. No. 5,233,097). In preparing these secondary synthesized materials it is preferred that the amount of substitute metal introduced which is not incorporated as framework oxide units be kept at a minimum. Excess surface or non-framework metal can cause rapid decomposition of the peroxide or otherwise interfere with the reaction. Examples of suitable zeolite molcular sieves for preparing the secondary synthesized zeolite catalysts employed in the present invention include erionite, mordenite, dinoptilolite, zeolite Y, zeolite L, zeolite LZ-105, zeolite omega, zeolite beta, zeolite TMA, offretite, zeolite ZSM-5, zeolite ZSM-12, zeolite ZSM-34, zeolite ZSM-35, and zeolite LZ-202. Both naturally occurring and synthetically prepared zeolites may be used. Suitable substitute metals include especially titanium, vanadium, iron, boron, chromium, beryllium, gallium, cobalt, zinc, haffnium, magnesium, manganese, and copper, especially e.g. titanium, vanadium, iron and copper and combinations thereof.

Primary synthesized zeolite-like metallosilicate catalysts according to the invention are synthetic materials such as mesoporous Ti-HMS and Ti-MCM as well as titanium silicalite materials such as TS-1 (a.k.a. zeolite MFI), TS-2 and VS-2. Ti-Al-β may also be mentioned. Suitable metals are as listed above with particular mention being made of titanium, vanadium, iron and combinations thereof. Further descriptions of primary synthesized zeolite-like metallosilicates can be found in the references cited herein. Vanadium containing aluminophosphates such as VAPO-5 may also be mentioned.

As suitable catalysts for use in the practice of this invention may be mentioned for example crystaline titanoaluminosilicate zeolites having a three-dimensional framework with $Si^{4+}$, $Ti^{4+}$ and $Al^{3+}$ in tetrahedral coordination with 4 oxygens, and where all of the oxygens in the tetrahedra are mutually shared between the tetrahedra silicon, titanium, or aluminum ions.

Zeolite Y is disclosed in U.S. Pat. No. 3,130,007; zeolite L is disclosed in U.S. Pat. No. 3,216,789; zeolite LZ-105 is disclosed in U.S. Pat. No. 4,257,885; zeolite omega is disclosed in U.S. Pat. No. 4,241,036; zeolite beta is disclosed in U.S. Patent No. 3,308,069; zeolite ZSM-5 is disclosed in U.S. Pat. No. 3,702,886; ZSM-12 is disclosed in is LaPierre et al. Zeolites 5 pp 346–348 (1985); zeolite ZSM-34 is disclosed in U.S. Pat. No. 4,086,186; zeolite ZSM-35 is disclosed in U.S. Pat. No. 3,992,466; mesoporous Ti-HMS and Ti-MCM-41 are disclosed in Tanev et al. Nature; 368, p 321–323 (1994); titanium silicalite TS-1 is disclosed in Romano et al. Chim. Ind 72 p 610–616 (1990); titanium silicalite TS-2 is disclosed in Reddy and Kuman, J. Catalysis 130, 440–446 (1991);); VS-2 is disclosed in Ramaswamy et al. Catal. Lett 22 (3) 239–249 (1993); Ti-Al-β is disclosed in Camblor et al., J. Chem. Soc. Chem. Commun. 1557 (1993); ferri-titanium-silicate (Fe-TS-1) and ferri-silicate (Fe-ZSM-5) are disclosed by Thangaraj et al. Applied Catalysis 57, L1-L3 (1991); Szostak et al. J. Catal. v. 600 555–557 (1986); Chu et al. J. Phys. Chem. v. 89 1569–71 (1985); cupric ion-exchanged Z. SM-5 is disclosed in Dessau, J. Catalysis 77, 304–306 (1982); VAPO-5 is disclosed in Montes et al. J. Phys. Chem. 94 6431–6435

(1990) (see also Collect Czech Chem Commun 57, 767–773 (1992)); U.S. Pat. No. 5,401,486 discloses alkali free titanium zeolite crystals; (for further zeolites cf also U.S. Pat. No. 5,098,687, U.S. Pat. No. 5,233,097 and U.S. Pat. No. 5,412,122).

As mentioned above the channels created in a catalyst during its preparation determine its suitability in the performance of the invention as the starting material should be capable of entering into the channels of the molecular sieve and this information may be applied by those skilled in the art to determine suitable catalysts for use in the present invention.

Preferred catalysts include secondary synthesized zeolites such as zeolites LZ102, LZ105, ZSM-5, ZSM-12, mordenite and zeolite Y each with titanium as substitute metal and primary synthesized zeolite like metallosilicates such as TS1 and TS2, mesoporous Ti-HMS, Ti-MCM-41 and V-MCM-41, VS-2 as well as Fe-ZSM-5.

Selectivity of catalysts containing exchangeable hydrogen ions may be improved if these are replaced by alkali or alkaline earth metal cations. Examples of cations which can be used to exchange the hydrogen include lithium, sodium, potassium, and cesium monocations and the dications of calcium, magnesium, beryllium, strontium, and barium. Catalysts where the exchangeable hydrogen ions are replaced by an alkali metal cation, especially sodium, potassium and in some cases lithium, are particularly preferred. Examples of catalysts according to the invention having such exchangeable hydrogen ions are those containing aluminum, especially secondary synthesized zeolites. The amount of alkali/alkaline earth metal exchanged is desirably sufficient to neutralize all the potential acid sites in the zeolite, which corresponds to the aluminum present. If the alkali/alkaline earth metal is designated as M, then the ratio M/Al=1 corresponds to complete neutralization of the acid sites and is the optimum amount of metal to be incorporated by exchange. Thus in this case optimum alkali/alkaline earth metal content varies with the aluminum content of the catalyst.

Alternatively or additionally, both activity and selectivity of the catalyst may be improved by calcination at a temperature between about 500° and about 750° C. Calcinations may be performed in air, nitrogen, carbon monoxide, or hydrogen, and it has been observed consistently that calcination in hydrogen affords a better catalyst than when calcination is performed at the same temperature in air, nitrogen, or carbon monoxide.

Alternatively or additionally selectivity may be improved by modifying the zeolite by treatment with a "selectivating agent" such as silicone e.g. in the form of phenylmethylsilicone. Such procedures are described e.g. in U.S. Pat. Nos. 5,321,183; 4,477,583; 4,465,886; 4,127,616 and U.S. Pat. No. 4,090,981, the contents of which in this respect are incorporated herein by reference.

Suitable oxidation agents included organic peroxides such as peroxycarboxylic acids, $RCO_3H$, alkyl hydroperoxides, ROOH, and dialkylperoxides, ROOR, for example peroxyacetic acid, peroxybenzoic acid, peroxyformic acid, t-butyl hydroperoxide, and di-t-butylperoxide and inorganic peroxides such as peroxydisulfuric acid. The preferred peroxide for use in the invention however, is hydrogen peroxide, especially in aqueous solution. Although 30% aqueous solutions $H_2O_2$ have been standard in the prior art the present process can be carried out at dilutions to 10% or less—e.g. 5%—with almost complete utilization of $H_2O_2$ and quantitative yields. Under certain conditions e.g. when employing aqueous solutions in the absence of other solvents dilutions as low as 0.1 to 1.0% e.g. 0.3% of $H_2O_2$ may be employed. Whilst the proportions of $H_2O_2$ to 1,4-dichlorobenzene may vary between 0.2 and 5, e.g. between 0.5 and 2. It has been determined that particularly high efficiency may be achieved using approximately equimolar amounts of $H_2O_2$ and 1,4-dichlorobenzene, e.g. ca 0.9 to ca 1.1 molar proportion of $H_2O_2$ per mole of 1,4-dichlorobenzene.

The use of solvents may also have a beneficial effect upon the process according to the invention. Suitable solvents may include alcohols, ketones and carboxylic acids, such as saturated alcohols having 1 to 4 carbon atoms, saturated ketones having up to 5 carbon atoms and saturated carboxylic acids with 2 to 6 carbon atoms; nitriles or even water. Examples include methanol, ethanol, isopropyl alcohol, acetone, methyl ethyl ketone, acetic acid, acetonitrile and water. Alternatively the process may be carried out in the absence of any solvent other than that used to dissolve the oxidizing agent e.g. water.

Depending on the solvent chosen use of phase transfer agents or surfactants to improve contact between 1,4-dichlorobenzene and the peroxide may be appropriate. In some cases an aqueous potassium acetate buffer may improve yield.

Under certain circumstances it may be desirable to have present in the starting mixture an amount of phenol or of the desired 2.5 dichlorophenol to facilitate the desired oxidation.

The process according to the invention may be carried out either on a batch basis or continuously. In batch operation catalysts may be employed in an amount of from ca 5 to ca 40 weight percent of the 1,4-dichlorobenzene to be hydroxylated. Reaction may be carried out in a sealed vessel under high pressure, e.g. 1000 p.s.i. nitrogen atmosphere. Reaction time is usually 24 hours or less and reaction temperatures of 10° to just below boiling point of the mixture are convenient. For example where water is the only solvent present temperatures of from 60° to 90° C. are appropriate. For example, the reaction may be carried out using hydrogen peroxide at a concentration of 0.1–35% e.g. 5 to 35% or 0.1 to 1% in the presence of catalyst at 10° to 60° or 60° to 100° in aqueous acetone or water respectively.

In continuous operation the reactants may be passed over a fixed bed of catalyst in as homogeneous a mixture as possible. Temperatures of from 10° to 100° are once again suitable and approximately equimolar proportions of hydrogen peroxide and 1,4-dichlorobenzene are preferred. In certain cases optimization of hydrogen peroxide usage and thus reduced loss through decomposition can be achieved by gradually adding the hydrogen peroxide in portions or continuously to the reaction mixture.

A preferred combination of these two modes of operation is batch recycling in which the reaction mixture of 1,4-dichlorobenzene and peroxide (e.g. $H_2O_2$), solvent and other components if used is passed over a fixed bed of catalyst to effect partial oxidation. The product is then recycled to pass repeatedly over the fixed bed to achieve virtually quantitative yields of the desired 1,5-dichlorophenol end product.

The starting material 1,4-dichlorobenzene has the formula

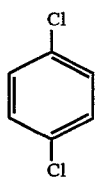

and is known, commercially available substance.

The desired end product 2,5-dichlorophenol has the formula

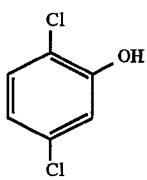

and is useful as an intermediate in the preparation of the commercial herbicide dicamba

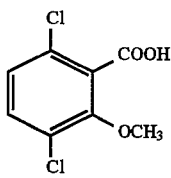

This process involves carboxylation of the 2,5-dichlorophenol to give 2-hydroxy-3,6-dichlorobenzoic and methylation of this substrate with subsequent saponification to give high purity dicamba.
(cf e.g. U.S. Pat. No. 3,013,054 for reaction from 2,5-dichlorophenol to dicamba).

The relevant portions of publications and other patent documents cited herein are hereby also incorporated by reference.

The following examples illustrate the invention. Temperatures are in degrees centigrade.

EXAMPLE 1

Preparation of Titanoaluminosilicates

These materials are prepared generally as described in U.S. Pat. No. 5,098,687. The titanosilicalite TS-1 is prepared as described in the literature. The following detailed descriptions for the preparation of Ti LZ-105 and Ti ZSM-5 are representative of the procedures followed.

a) Preparation of Titanium Substituted LZ-105 (Ti LZ-105)

Ammonium exchanged LZ-105, 500 g on an anhydrous basis is added to 5 l deionized water and heated to 70° C. $(NH_4)_2TiF_6$, 78.9 gm is added to the zeolite slurry in increments; 26.3 gm initially, 26.3 gm after 10 minutes, and 26.3 gm after 20 minutes. After the final addition of the fluorotitanate salt, the slurry is heated to 95° C. and held for 66 hours. The slurry is filtered hot and washed well with hot deionized water until the filtrate tests negative for residual fluoride by addition of $CaCl_2$ to the filtrate.

b) Preparation of Titanium Substituted ZSM-5 (Ti ZSM-5)

Ammonium exchanged ZSM-5, 100 g on an anhydrous basis, is added to 400 mL deionized water and heated to 70° C. 10.4 gm of $(NH_4)_2TiF_6$ is added at once. After the addition of the fluorotitanate salt the slurry is heated to 95° C. and held for 24 hours. The slurry is filtered hot and washed well with hot deionized water until the filtrate tests negative for residual fluoride by addition of $CaCl_2$ to the filtrate.

c) Potassium Exchange of Titanium Substituted ZSM-5

The Ti-ZSM-5 obtained above is exchanged three times at reflux with excess KCl salt solution to remove all acidic properties of the zeolite.

EXAMPLE 2

Oxidation of 1,4-Dichlorobenzene a) To a solution of 14.7 g (0.1 mole) of 1,4-dichlorobenzene dissolved in 60 ml of acetone is added with stirring 40 weight percent catalyst (based on 1,4-dichlorobenzene) followed by 11.3 ml of 30% hydrogen peroxide (equimolar quantities of 1,4-dichlorobenzene and hydrogen peroxide). After 24 hours at 20° the catalyst is removed by filtration, and washed with acetone. The combined filtrates are treated dropwise with concentrated aqueous sodium bisulfite to destroy any residual hydrogen peroxide and the solvents are removed in vacuo to give the desired product. This may be purified e.g. by vacuum distillation (b.p. 70° C. at 2 mm pressure) to give 2,5-dichlorophenol, m.p. 57°–59° C.

b) Under the batch recycle conditions, 14.7 g of 1,4-dichlorobenzene is dissolved in 100 ml of acetone and 11.3 ml of 30% hydrogen peroxide followed by 20 ml of water are added. This solution is then repeatedly passed over a bed of the catalyst.

c) To a suspension of 10 mg of 1,4-dichlorobenzene (0.07 mmol) in 1 ml of 0.3% aqueous hydrogen peroxide is added with stirring 100 weight percent of Ti-ZSM-5 (based on 1,4-dichlorobenzene). The reaction vessel is sealed and heated at 85° for 24 hours. The reaction is then cooled to 2345° and the catalyst removed by filtration and washed with methanol or acetone.

d) To a suspension of 50 mg of 1,4-dichlorobenzene (0.34 mmol) in 3 ml of 30% aqueous hydrogen peroxide is added with stirring 100 weight percent catalyst (based on 1,4-dichlorobenzene). The reaction vessel is sealed and heated at 85° for 24 hours. The reaction is then cooled to 23°–25° and the catalyst removed by filtration and washed with methanol or acetone.

Further details of preparation of catalysts reactants and reaction conditions useful in carrying out the process according to the invention can be found in U.S. Pat. No. 5,233,097 the contents of which are incorporated herein by reference.

We claim:

1. A process for the preparation of 2,5-dichlorophenol which comprises selectively oxidizing 1,4-dichlorobenzene using peroxide in the presence of a catalyst selected from the group consisting of a secondary synthesized zeolite or zeolite-like metallosilicate; a primary synthesized zeolite-like metallosilicate; and an aluminophosphate based molecular sieve.

2. A process according to claim 1 wherein the secondary synthesized zeolite is selected from the group consisting of erionite, mordenite, clinoptilolite, zeolite Y, zeolite L, zeolite LZ-105, zeolite omega, zeolite beta, zeolite TMA, offretite, zeolite ZSM-5, zeolite ZSM-12, zeolite ZSM-34, zeolite ZSM-35, and zeolite LZ-202.

3. A process according to claim 1 wherein the metallosilicate includes an ion selected from the group consisting of titanium, vanadium, iron, boron, chromium, beryllium, gallium, cobalt, zinc, haffnium, magnesium, manganese and copper.

4. A process according to claim 3 wherein the ion is selected from the group consisting of titanium, vanadium, iron and copper.

5. A process according to claim 1 wherein the primary synthesized zeolite-like metallosilicate is selected from the group consisting of mesaporous Ti-HMs and Ti-MCM and a titanium silicalite.

6. A process according to claim 1 wherein the catalyst is selected from the group of zeolites consisting of LZ102, LZ105, ZSM-5, ZSM-12, mordenite and zeolite Y each with titanium as a substitute metal and TS1, TS2, mesoperous Ti-HNS,Ti-MCM-41, V-MCM-41, VS-2 and Fe-ZSM-5.

7. The process of claim 1 wherein the peroxide is selected from the group consisting of hydrogen peroxide, peroxycarboxylic acids, alkyl hydroperoxides, dialkylperoxides, and peroxydisulfuric acid.

8. The process of claim 7 wherein the peroxide is hydrogen peroxide.

9. The process of claim 1 wherein the peroxide and the 1,4-dichlorobenzene are reacted in a solvent.

10. The process of claim 9 wherein the solvent is selected from the group consisting of saturated alcohols having 1 to 4 carbon atoms, saturated ketones having up to 5 carbon atoms, and saturated carboxylic acids with 2 to 6 carbon atoms.

11. The process of claim 8 wherein hydrogen peroxide is used as an aqueous solution containing not more than 10 weight percent hydrogen peroxide and no other solvent is present.

12. The process of claim 11 wherein hydrogen peroxide is used as an aqueous solution containing not more than 5 weight percent hydrogen peroxide.

13. The process of claim 8 wherein hydrogen peroxide is present in from about 0.2 to about 5 molar proportions relative to the 1,4-dichlorobenzene.

14. The process of claim 13 wherein hydrogen peroxide is present in from about 0.5 to about 2 molar proportions relative to 1,4-dichlorobenzene.

15. The process of claim 14 wherein hydrogen peroxide is present in from about 0.9 to about 1.1 molar proportions relative to 1,4-dichlorobenzene.

16. The process of claim 1 further characterized in that the catalyst is calcined in hydrogen at a temperature from about 500° to about 750° C.

17. The process of claim 1 further characterized in that the exchangeable hydrogen ions of the catalyst if present are replaced by an alkali or alkaline earth metal cation.

18. The process of claim 17 wherein the exchangeable hydrogen ions of the catalyst if present are replaced by an alkali metal cation.

19. The process of claim 18 wherein the alkali metal cation is sodium or potassium.

20. The process of claim 17 wherein the amount of alkali or alkaline earth metal cation exchanged is sufficient to neutralize all the potential acid sites in the catalyst.

* * * * *